US010227642B2

(12) United States Patent
Fischer et al.

(10) Patent No.: US 10,227,642 B2
(45) Date of Patent: Mar. 12, 2019

(54) DETERGENT FREE POLYMERASES (71) Applicant: ROCHE DIAGNOSTICS OPERATIONS, INC., Indianapolis, IN (US)

(72) Inventors: Ulrike Fischer, Penzberg (DE); Michael Greif, Penzberg (DE); Harald Sobek, Penzberg (DE); Johann-Peter Thalhofer, Weilheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/160,453

(22) Filed: Jan. 21, 2014

(65) Prior Publication Data
US 2014/0134633 A1 May 15, 2014

Related U.S. Application Data (63) Continuation of application No. 13/042,628, filed on Mar. 8, 2011.

(30) Foreign Application Priority Data

Apr. 12, 2010 (EP) .................... 10159673

(51) Int. Cl.
C12Q 1/68 (2018.01)
C12P 19/34 (2006.01)
C12Q 1/686 (2018.01)
C12N 9/12 (2006.01)

(52) U.S. Cl.
CPC ........... *C12Q 1/686* (2013.01); *C12N 9/1252* (2013.01)

(58) Field of Classification Search
CPC .............. C12Q 1/686; C12Q 2521/101; C12Q 2521/137; C12N 9/1252
See application file for complete search history.

(56) References Cited

U.S. PATENT DOCUMENTS

| 4,420,072 | A | 12/1983 | Treffinger et al. |
| 5,118,801 | A | 6/1992 | Lizardi et al. |
| 5,127,155 | A | 7/1992 | Kendic |
| 5,210,015 | A | 5/1993 | Gelfand et al. |
| 5,487,972 | A | 1/1996 | Gelfand et al. |
| 5,538,848 | A | 7/1996 | Livak et al. |
| 5,677,152 | A | 10/1997 | Birch et al. |
| 5,773,258 | A | 6/1998 | Birch et al. |
| 5,804,375 | A | 9/1998 | Gelfand et al. |
| 5,814,506 | A | 9/1998 | Kong et al. |
| 6,020,130 | A | 2/2000 | Gold et al. |
| 6,174,670 | B1 | 1/2001 | Wittwer et al. |
| 2005/0037412 | A1 | 2/2005 | Meier et al. |
| 2011/0008846 | A1* | 1/2011 | Peters et al. ............ 435/91.2 |

FOREIGN PATENT DOCUMENTS

| EP | 0359006 A1 | 3/1990 | |
| EP | 0757100 A1 | 2/1997 | |
| WO | 1989/006691 A2 | 7/1989 | |
| WO | 1997/035988 A1 | 10/1997 | |
| WO | 1997/046707 A3 | 12/1997 | |
| WO | 1997/046712 A3 | 12/1997 | |
| WO | 1997/046714 A1 | 12/1997 | |
| WO | 2003/089606 A3 | 10/2003 | |
| WO | 2008/013885 A3 | 1/2008 | |
| WO | WO 2008013885 A2 * | 1/2008 | ............ C12Q 1/686 |
| WO | 2008/077017 A3 | 6/2008 | |
| WO | WO-2008152102 A1 * | 12/2008 | .......... C12N 9/1252 |
| WO | WO 2009083424 A2 * | 7/2009 | |

OTHER PUBLICATIONS

Chiou et al., "A Closed-Cycle Capillary Polymerase Chain Reaction Machine," Analytical Chemistry, 2001, vol. 73, pp. 2018-2021.*
Nitsche et al., "Different Real-Time PCR Formats Compared for the Quantitative Detection of Human Cytomegalovirus DNA," Clinical Chemistry, 1999, vol. 45, No. 11, pp. 1932-1937.*
FERMENTAS UAB (GB 0915796.7, published Oct. 2009).*
LC Red 640 Roche Product Safety Data Sheet [Retrieved on-line: https://pim-eservices.roche.com/SDS/US/en/12015161001; retrieval date Dec. 15, 2016, pp. 1-9].*
Ho et al., "Rapid quantification of hepatitis B virus DNA by real-time PCR using fluroescent hybridization probes," Journal of Medical Microbiology, 2003, vol. 52, pp. 397-402.*
Yamagami et al., "Mutant Taq DNA polymerases with improved elongation ability as a useful reagent for genetic engineering," Frontiers in Microbiology, vol. 5, pp. 1-10 (Year: 2014).*
European Search Report dated Aug. 8, 2010 in Application No. EP10159673.2.
Bernard, Philip S. et al., Integrated Amplification and Detection of the C677T Point Mutation in the Methylenetetrahydrofolate Reductase Gene by fluorescence Resonance Energy Transfer and Probe Melting Curves, Analytical Biochemistry, 1998, pp. 101-107, vol. 255.
Engelke, David R. et al., Purification of Thermus aquaticus DNA Polymerase Expressed in *Escherichia coli*, Analytical Biochemistry, 1990, pp. 396-400, vol. 191.
Grimm, Edith and Arbuthnot, Patrick, Rapid purification of recombinant Taq DNA polymerase by freezing and high temperature thawing of bacterial expression cultures, Nucleic Acids Research, 1995, pp. 4518-4519, vol. 23, No. 21.
Lawyer, Frances C. et al., Isolation, Characterization, and Expression in *Escherichia coli* of the DNA Polymerase Gene from Thermus aquaticus, The Journal of Biological Chemistry, Apr. 15, 1989, pp. 6427-6437, vol. 264, No. 11.
Lawyer, Frances C. et al., High-level Expression, Purification, and Enzymatic Characterization of Full-length Thermus aquaticus DNA Polymerase and a Truncated Form Deficient in 5' to 3' Exonuclease Activity, PCR Methods and Applications, May 1993, pp. 275-287, vol. 2, No. 4.

(Continued)

*Primary Examiner* — Young J Kim
(74) *Attorney, Agent, or Firm* — Faegre Baker Daniels LLP (57) ABSTRACT The present invention relates to a formulation of a thermostable DNA polymerase which is completely free of detergents and its particular use in real time polymerase chain reaction (PCR). Such a formulation may be obtained if the selected purification method does not require the addition of a detergent at any purification step.

4 Claims, 3 Drawing Sheets

Specification includes a Sequence Listing.

(56) References Cited

OTHER PUBLICATIONS

Matthews, Jayne A. and Kricka, Larry J., Analytical Strategies for the Use of DNA Probes, Analytical Biochemistry, 1988, pp. 1-25, vol. 169.

Moretti, Tamyra et al., Enhancement of PCR Amplification Yield and Specificity Using AmpliTaq Gold(tm) DNA Polymerase, BioTechniques, Oct. 1998, pp. 716-722, vol. 25.

Wilson, Ian G., Inhibitation and Facilitation of Nucleic Acid Amplification, Applied and Environmental Microbiology, Oct. 1997, pp. 3741-3751, vol. 63, No. 10.

Kim, Yun Jae et al., "Cloning, Purification, and Characterization of a New DNA Polymerase from a Hyperthermophilic Archaeon, *Thermococcus* sp. NA1," Journal of Microbiology and Biotechnology, 2007, pp. 1090-1097, vol. 17, No. 7.

New England Biolabs, Inc., Aug. 2007 Catalogue & Technical Reference, 2007, p. 100.

* cited by examiner

Figure 1

Figure 1: Taq DNA Polymerase (detergent free)
A = 300 ng, B = 30 ng, C = 3 ng, D = 0,3 ng, E = 0,03 ng, F = NTC

Figure 2

Figure 2: Taq DNA Polymerase
A = 300 ng, B = 30 ng, C = 3 ng, D = 0,3 ng, E = 0,03 ng, F = NTC

Figure 3

Crossing point

Figure 3: Taq DNA Polymerase

A = 300 ng, B = 30 ng, C = 3 ng, D = 0,3 ng, E = 0,03 ng, F = NTC

DETERGENT FREE POLYMERASES

RELATED APPLICATIONS

This application is a continuation of U.S. patent application Ser. No. 13/042,628, filed on Mar. 8, 2011, which claims priority to European Patent Application EP 10159673.2 filed Apr. 12, 2010. Each of these applications is hereby incorporated by reference in its entirety.

SEQUENCE LISTING

The instant application contains a Sequence Listing which has been submitted in ASCII format via EFS-Web and is hereby incorporated by reference in its entirety. Said ASCII copy, created on Feb. 23, 2011, is named 26670US.txt, and is 1,765 bytes in size.

FIELD OF THE INVENTION

The present invention relates to the technical field of preparation and application of thermostable DNA polymerases. More precisely, the present invention relates provides a new method for production and use of thermostable DNA polymerases without any addition of detergent during production, storage or during application of the enzyme.

BACKGROUND OF THE INVENTION

Thermostable DNA polymerases are enzymes which have been isolated and recombinantly expressed for a long time since the establishment of the polymerase chain reaction (PCR). However as it is the case for other enzymatical reactions, also the performance of PCR is known to be at least partially hampered by the presence of trace amounts various different reagents such as detergents. On the other hand, the presence of detergents is known to be essential for many polymerase purification protocols and long term stabilization of enzymes in general and DNA polymerases in particular.

Lawyer, F. C. et al. (JBC 264 (1989) 6427-6434) for the first time disclose the cloning and recombinant expression of Taq DNA polymerase. Similarly, U.S. Pat. No. 5,127,155 discloses polymerase formulations which are stabilized with non ionic detergents which are particularly useful for PCR applications. Typical detergents stabilizing detergents used are TRITON X-100 (Union Carbide Chemicals & Plastics Technology Corporation), TWEEN 20 (ICI Americas Inc.) and NONIDET P-40 (Shell International Petroleum Company Limited).

Morever, according to the observations of the inventors of U.S. Pat. No. 5,127,155, the presence of detergents within the disclosed formulations is not only required to maintain enzyme stability, but also to enhance the activity of the polymerase.

Alternative purification methods and formulations have been disclosed. For example, WO 08/077,017 discloses polymerase formulations with anionic and zwitter-ionic detergents instead of non ionic detergents.

Lawyer et al. (PCR Methods and Applications, Cold Spring Harbor, p. 275-287 (1993)) provide improved protocols, wherein the presence of detergents during purification of the enzyme is reduced. Engelke, D. R. et al. (Anal. Biochem. 191 (1990) 396-400) disclose formulations of recombinant Taq polymerase with only trace amounts of detergent, because the finally added storage buffer is free of detergent compounds.

In view of the outlined prior art, it was an object of the present invention to provide an improved polymerase formulation with optimized performance in a polymerase chain reaction (PCR).

SUMMARY OF THE INVENTION

Thus, the present invention provides a formulation of a thermostable DNA polymerase which is completely free of detergents. Such a formulation may be obtained, if the selected purification method does not require the addition of a detergent at any purification step.

The present invention also provides a kit comprising a thermostable DNA polymerase formulation which is completely free of detergents or a reaction mixture comprising a thermostable DNA polymerase which is completely free of detergents.

In addition, the present invention is directed to the use of the inventive polymerase formulations as disclosed above. Such formulations are predominantly advantageous, when they are used for the amplification of a target nucleic acid by means of a PCR, preferably real time PCR and most preferably real time PCR, wherein the amplification product is detected by at least one pair of FRET hybridization probes.

Furthermore, the present invention provides a method for preparation of a thermostable DNA polymerases, wherein all steps of preparation are executed in the absence of any detergent.

For example, such a method may comprise the following steps:
a) providing a lysate supplemented with protease inhibitors,
b) ammonium sulfate precipitation
c) a first chromatographic separation using a first affinity chromatography matrix
d) a second chromatographic separation using a second affinity chromatography matrix
e) a third chromatographic separation using a Hydroxyapatite matrix.

Alternatively, such a method may require that the thermostable DNA polymerase is recombinantly expressed in the form of a fusion protein which comprises a His tag. Then the preparation comprises the step of purifying said fusion protein using a nickel-loaded ion affinity column.

DETAILED DESCRIPTION OF THE INVENTION

The present invention is originating from the theoretical hypothesis that for some the enzymatic activity of trace amounts of detergents might somehow affect the performance of thermostable DNA polymerases under at least some specific conditions. As it will be shown in the examples, the hypothesis could actually be tested to be true.

Enzyme Formulations

Therefore, in a first aspect, the present invention provides a formulation of a thermostable DNA polymerase which is completely free of detergents. In the context of the present invention, the term "formulation of a thermostable DNA polymerase" is being understood as any preparation of an at least partially purified thermostable DNA polymerase, which has been isolated from a cell lysate. The lysate may be obtained from organisms which naturally contain said thermostable DNA polymerase, or preferably from recombinantly modified host cells, which express the gene encoding said thermostable DNA polymerase.

Thermostable DNA polymerases are thermostable enzymes which have originally been isolated and cloned from thermophilic bacteria. These enzymes catalyze the template dependent primer extension by means of creating a phosphodiester bond between the free 3' OH group of said primer and the alpha-phosphate moiety of a desoxynucleotide, whereas pyrophosphate is simultaneously generated as a side product. Preferably, said template is a DNA template. Alternatively, the template may be RNA.

The most prominent example of a thermostable DNA dependent DNA polymerase is Taq DNA Polymerase originating from Thermos aquaticus. It possesses two enzymatic activities: a 5'-3' polymerase activity and a double-strand specific 5'-3' exonuclease activity, which provides the enzyme with strand displacement capability.

A great variety of thermostable DNA polymerases can be formulated according to the present invention. Preferably, the thermostable DNA polymerase is selected from a group consisting of *Aeropyrum pernix, Archaeoglobus fulgidus, Desulfurococcus* sp. Tok., *Methanobacterium thermoautotrophicum, Methanococcus* sp. (e.g., *jannaschii, voltae*), *Methanothermus fervidus., Pyrococcus* species (*furiosus*, species GB-D, *woesii, abyssi, horikoshii*, KOD), *Pyrodictium abyssii, Pyrodictium occultum, Sulfolobus* sp. (e.g. *acidocaldarius, solfataricus*), *Thermococcus* species (*zilligii, barossii, fumicolans, gorgonarius*, JDF-3, *kodakaraensis* KODI, *litoralis*, species 9 degrees North-7, species JDF-3, *gorgonarius*, TY), *Thermoplasma acidophilum, Thermosipho africanus, Thermotoga* sp. (e.g., *maritima, neapolitana*), *Methanobacterium thermoautotrophicum, Thermus* species (e.g., *aquaticus, brockianus, filiformis, flavus, lacteus, rubens, ruber, thermophilus*, ZO5.

In one embodiment, the thermostable DNA polymerase is a DNA template dependent polymerase. In another embodiment, the thermostable DNA polymerase has additional reverse transcriptase activity and may be used for RT-PCR. One example for such enzyme is Tth DNA polymerase from *Thermus thermophilus* (Roche Diagnostics Cat. No. 11 480 014 001).

Many thermostable DNA dependent DNA polymerases such as Taq DNA polymerase lack double strand dependent 3'-5' exonuclease activity which is also known as proofreading activity. Yet, the scope of the present invention also includes other themostable enzymes which possess such a proofreading activity such as Pwo Polymerase (Roche Applied Science Cat. No. 04 743 750 001), Tgo Polymerase and Pfu Polymerase.

Also within the scope of the present invention are mutants, variants or derivatives thereof, chimeric or "fusion-polymerases", e.g., Phusion (Finnzymes or New England Biolabs, Cat. No. F-530S) or iProof (Biorad, Cat. No. 172-5300), Pfx Ultima (Invitrogen, Cat No. 12355012) or Herculase IT Fusion (Stratagene, Cat. No. 600675). Furthermore, compositions according to the present invention may comprise blends of one or more of the polymerases mentioned above.

The thermostable DNA polymerase also may be reversibly inactivated as a result of a chemical modification. More precisely, heat labile blocking groups are introduced into the Taq DNA polymerase which renders the enzyme inactive at room temperature (U.S. Pat. No. 5,773,258). These blocking groups are removed at high temperature during a pre-PCR step such that the enzyme is becoming activated. Such a heat labile modification, for example can be obtained by coupling citraconic anhydride or aconitric anhydride to the lysine residues of the enzyme (U.S. Pat. No. 5,677,152). Enzymes carrying such modifications are meanwhile commercially available as Amplitaq Gold (Moretti, T., et al., Biotechniques 25 (1998) 716-22) or FastStart DNA polymerase (Roche Applied Science Cat. No. 04 738 284 001).

In a specific embodiment, said thermostable DNA polymerase according to the present invention is either Taq DNA polymerase or delta 288 Taq DNA polymerase as disclosed in US 2005/0037412 or said delta 288 Taq DNA polymerase associated with an aptamer as disclosed in U.S. Pat. No. 6,020,130.

Ideally, a formulation of a thermostable DNA polymerase which is completely free of detergents is obtained by a purification method which does not require the addition of a detergent at any purification step. After a sufficient degree of purification is obtained, the formulation may comprise a buffer system and other non detergent supplements. Such a formulation may comprise one, several or all of the following components: Tris-buffer, EDTA, DTT, salt and glycerol. For example, such a formulation may comprise on, several or all of the following amounts of components: 10 to 50 mM Tris/HCl pH 7.5, 0.05-0.2 mM EDTA, 0, 5-2 mM DTT, 50-200 mM potassium chloride, and 20-80% glycerol.

Kits

In a second aspect of the present invention, any of the inventive polymerases disclosed above may be a component of a kit. In a simple embodiment, such a kit may comprise only said formulation and a reaction buffer in which a respective polymerization reaction can efficiently take place. Optionally, such a kit in addition may comprise one or several desoxynucleoside-triphosphates such as dATP, dGTP, dCTP, and/or dTTP or derivatives or analogs thereof.

In a more elaborate embodiment, such a kit may comprise additional reagents for performing a primer extension reaction in general or a polymerase chain reaction (PCR) in particular. For example, such a kit in addition may comprise at least one primer which is capable of binding a nucleic acid template that shall be amplified. In case of a PCR kit, said kit may comprise one or several primer pairs, each designed to amplify a specific fragment of the template DNA. Alternatively, if the kit is designed for random amplification methods such as but not being limited to whole genome or whole transcriptome amplification applications, the primer component may be a pool of oligonucleotides with an at least partially randomized sequence.

In another embodiment, which is compatible with the previous one, the kit according to the present invention may comprise additional reagents which enable the detection of the products generated by the thermostable DNA polymerase. In particular, these reagents may enable the detection of a PCR amplification product by means of real time PCR.

Respective kits according to the present invention may thus additionally may comprise a double strand specific fluorescent DNA binding agent such as SYBR Green (Molecular Probes, Inc., Invitrogen Cat. No. 4304886) or LC480 Resolight dye (Roche Applied Science Cat. No. 04 909 640 001). Alternatively, respective kits according to the present invention may comprise labeled hybridization probes such as TaqMan hydrolysis probes (U.S. Pat. No. 5,804,375) or Molecular Beacons (U.S. Pat. No. 5,118,801). In a particular embodiment, respective kits comprise at least on or several pairs of FRET hybridization probes (U.S. Pat. No. 6,174,670).

Reaction Mixtures

In a third aspect of the present invention, any of the inventive polymerase formulations may be part of a reaction mixture for performing a template dependent primer extension reaction in general and PCR amplification reaction in particular. In its broadest meaning, such a reaction mixture which is free of any trace amounts of detergent comprises a polymerase formulation free of any detergent, obtainable by methods as disclosed in the examples
a template nucleic acid, which is preferably a DNA
at least one primer, which is an oligonucleotide that is capable of binding to said DNA, and
at least one desoxynucleotide triphosphate or any analog or derivative thereof, but preferably 4 dNTPs, i.e., dATP, dCTP, dGTP, and dTTP, or dUTP instead of dTTP.

In one embodiment, such a reaction mixture is a PCR reaction mixture free of any detergent and comprises a formulation of a thermostable DNA polymerase that is completely free of detergents
a template nucleic acid, which is preferably a DNA
at least one or several pairs of amplification primers, designed in such a way that that a specific region of target DNA is amplified from the template nucleic acid, and
the deoxynucleotide triphosphates dATP, dCTP, dGTP, and dTTP/or dUTP.

In a particular embodiment, such PCR reaction mixtures may additionally comprise any additional reagents which are enable the detection of the products generated by the thermostable DNA polymerase in real time. Respective mixtures according to the present invention may thus additionally may comprise double strand specific fluorescent DNA binding agents, TaqMan hydrolysis probes, Molecular Beacons or FRET hybridization probes, which have already been disclosed above.

Methods of Use

The inventive thermostable DNA polymerase formulations without any detergents are useful for any type of nucleic acid amplification reaction. In one embodiment, they may be used for random amplification such as a random priming reaction or whole genome amplification. In a particular embodiment, said inventive formulations are particularly useful for amplification of a specific target nucleic acid by means of performing a PCR reaction, which may be a real time PCR reaction.

For analytical purposes, such a PCR reaction may be monitored in real time. Within real time PCR, sample analysis occurs concurrently with amplification in the same tube within the same instrument. The formation of PCR products is monitored in each cycle of the PCR. It is usually measured in thermocyclers which have additional devices for measuring fluorescence signals during the amplification reaction. DNA dyes or fluorescent probes can be added to the PCR mixture before amplification and used to analyze PCR products during amplification. This combined approach decreases sample handling, saves time, and greatly reduces the risk of product contamination for subsequent reactions, as there is no need to remove the samples from their closed containers for further analysis.

Therefore, in a fourth aspect, the present invention is also directed to the use of a formulation of a thermostable DNA polymerase that is completely free of detergents for the amplification by means of PCR and in particular real time PCR.

In one embodiment, since the amount of double stranded amplification product usually exceeds the amount of nucleic acid originally present in the sample to be analyzed, double-stranded DNA specific dyes may be used, which upon excitation with an appropriate wavelength show enhanced fluorescence only if they are bound to double-stranded DNA. Preferably, only those dyes may be used which like SYBR Green I, for example, do not affect the efficiency of the PCR reaction.

Alternatively, fluorescence labeled hybridization probes which only emit fluorescence upon binding to its target nucleic acid can be used.

In another embodiment, a single-stranded hybridization probe is labeled with two components. When the first component is excited with light of a suitable wavelength, the absorbed energy is transferred to the second component, the so-called quencher, according to the principle of fluorescence resonance energy transfer. During the annealing step of the PCR reaction, the hybridization probe binds to the target DNA and is degraded by the 5'-3' exonuclease activity of the Taq DNA polymerase during the subsequent elongation phase. As a result the excited fluorescent component and the quencher are spatially separated from one another and thus a fluorescence emission of the first component can be measured. TaqMan hydrolysis probe assays are disclosed in detail in U.S. Pat. No. 5,210,015, U.S. Pat. No. 5,538,848, and U.S. Pat. No. 5,487,972. TaqMan hybridization probes and reagent mixtures are disclosed in U.S. Pat. No. 5,804,375.

In a further embodiment, Molecular Beacon hybridization probes are labeled with a first component and with a quencher, the labels preferably being located at both ends of the probe. As a result of the secondary structure of the probe, both components are in spatial vicinity in solution. After hybridization to the target nucleic acids both components are separated from one another such that after excitation with light of a suitable wavelength the fluorescence emission of the first component can be measured (U.S. Pat. No. 5,118,801).

In a still further particular embodiment, a formulation of a thermostable DNA polymerase that is completely free of detergents is used for amplification of a target nucleic acid by means of a PCR, characterized in that said real time PCR is monitored in real time by means of FRET hybridization probes.

The FRET hybridization probe test format is useful for all kinds of homogenous hybridization assays (Matthews, J. A., and Kricka, L. J., Analytical Biochemistry 169 (1988) 1-25). It is characterized by two single-stranded hybridization probes which are used simultaneously and are complementary to adjacent sites of the same strand of the amplified target nucleic acid. Both probes are labeled with different fluorescent components. When excited with light of a suitable wavelength, a first component transfers the absorbed energy to the second component according to the principle of fluorescence resonance energy transfer such that a fluorescence emission of the second component can be measured when both hybridization probes bind to adjacent positions of the target molecule to be detected. Alternatively to monitoring the increase in fluorescence of the FRET acceptor component, it is also possible to monitor fluorescence decrease of the FRET donor component as a quantitative measurement of hybridization event.

In particular, the FRET hybridization probe format may be used in real time PCR, in order to detect the amplified target DNA. Among all detection formats known in the art of real time PCR, the FRET hybridization probe format has been proven to be highly sensitive, exact and reliable (U.S. Pat. No. 6,174,670). As an alternative to the usage of two FRET hybridization probes, it is also possible to use a fluorescent-labeled primer and only one labeled oligonucleotide probe (Bernard, P. S., et al., Analytical Biochemistry 255 (1998) 101-107). In this regard, it may be chosen arbitrarily, whether the primer is labeled with the FRET donor or the FRET acceptor compound.

Similar to other probe based detection formats, also the FRET hybridization probe detection format can be "multiplexed". More precisely, in one reaction vessel, multiple targets may become amplified with multiple pairs of amplification primers and detected with multiple hybridization probes. In this case, said multiple probes are labeled with different detectable fluorescent dyes in order to detect and discriminate the multiple targets which are supposed to be found in the sample.

For multiplex detection with the FRET hybridization probe format, it is possible that fluorescein or fluorescein derivatives are used as a FRET donor moiety in combination with different FRET acceptor moieties such as Cy-5, LC-Red-640, or LC-red 705.

A typical example for an instrument capable of performing multiplex real time PCR is the Roche Diagnostics LIGHTCYCLER (Cat. No. 3 531 414 201). It is a fast PCR system enabling kinetic on-line PCR quantification and subsequent analysis of PCR-product melting curves. The optical system of the current LIGHTCYCLER version 2.0 being commercially available contains one light source, a blue light emitting diode (470 nm LED) and six detection channels. A defined signal threshold is determined for all reactions to be analysed and the number of cycles Cp required to reach this threshold value is determined for the target nucleic acid as well as for the reference nucleic acids such as the standard or housekeeping gene. The absolute or relative copy numbers of the target molecule can be determined on the basis of the Cp values obtained for the target nucleic acid and the reference nucleic acid.

The fluorescence emitted by a sample is separated by a set of dichroic mirrors and filters into different wavelengths that can be recorded in one of the six detection channels. Due to the fluorescent compounds which are available on the market, this allows detection of the double-stranded DNA-binding dye SYBR Green 1, dual color detection with the TaqMan Probe format and 4-color detection with the Hybridization Probe (HybProbe) format. Details of the LIGHTCYCLER system are disclosed in WO 97/467(7, WO 97/46712 and WO 97/46714.

However, at late stages of FRET based real time PCR assays, and in particular respective multiplex assays, a decrease in fluorescence is frequently observed. This drawback of conventional real time PCR using FRET hybridization probes is called "hook" effect. Examples are given in FIGS. 2 and 3. Surprisingly, this effect can be eliminated, if a polymerase formulation according to the present invention is used and the reaction mixture is free of any trace amounts of detergent.

Preparation Methods

In a fifth aspect, the present invention provides a method for preparation of a thermostable DNA polymerases, characterized in that all steps of preparation are executed in the absence of any detergent. Generally speaking, any preparation method which can be successfully implemented for purification of a thermostable DNA polymerase without any addition of a detergent in each of the steps necessary can be applied.

For example, such a purification method can comprise the steps of
  a) providing a lysate supplemented with protease inhibitors,
  b) ammonium sulfate precipitation
  c) a first chromatographic separation using a first affinity chromatography matrix
  d) a second chromatographic separation using a second affinity chromatography matrix
  e) a third chromatographic separation using a Hydroxyapatite matrix.

The lysate is preferentially derived from a recombinant prokaryotic cell, such as *E. coli*, which is genetically modified to express the gene encoding the desired thermostable DNA polymerase in high yield. After harvesting the cells from a fermentation medium by means of centrifugation, the pellet may be frozen and in the sate, cells may be disrupted by physical methods such as sonication or, preferably by treatment with a French pressure cell. Prior, during, or immediately after lysis, a buffer may be added which already contains appropriate protease inhibitors such as, e.g., PMSF Leupeptin and the like.

Parallel to the step of ammonium sulfate precipitation, nucleic acids contained in the lysate may be removed, either enzymatically or preferably by means of precipitation, for example with Polymin P. Both, nucleic acid precipitates and protein precipitates may be removed by centrifugation.

The supernatant may then be subjected to a first chromatographic step, using an affinity chromatographic column, which is preferably functioning according to the principle of hydrophobic interaction chromatography. Most preferably, the affinity matrix is a Phenyl-SEPHAROSE, such as Phenyl-SEPHAROSE CL-4B (GE Healthcare Bio-Sciences).

Subsequently, a second affinity chromatography may be performed using a second affinity matrix which is different from the first affinity matrix. For example, the sample may be purified over a Heparin SEPHAROSE column, containing Heparin SEPHAROSE CL-6B.

Afterwards, further purification may be achieved by means of a third chromatographic step which is preferably purification by means of hydroxyapatite chromatography.

A simplified purification protocol is possible, if the recombinantly expressed thermostable DNA polymerase comprise a so called Poly-His-tag. Polyhistidine-tags are often used for affinity purification of Polyhistidine-tagged recombinant proteins expressed in prokaryotic and other expression systems. The recombinant bacterial cells are harvested via centrifugation and the resulting cell pellet lysed, e.g., by physical means under conditions as disclosed above.

At this stage the crude extract contains the recombinant protein among several other proteins and nucleic acids originating from the bacterial host. Optionally, nucleic acids contained in the sample at this stage may be digested by DNAse I.

The mixture is then loaded onto a column comprising a specific affinity matrix such as nickel or cobalt loaded SEPHAROSE or the like. A respective SEPHAROSE or agarose matrix contains bound nickel or cobalt ions to which the polyhistidine-tag binds with high affinity. The resin is subsequently washed with a buffer to remove other proteins that do not specifically interact with the cobalt or nickel ion.

Subsequently, further purification may be achieved by means of a second chromatographic step, which is preferably an anion exchange chromatography. For example, a Q-SEPHAROSE ff column may be used.

Thus, a typical purification method for purifying his-tagged thermostable DNA polymerases may comprise the steps of
 a) providing a lysate of frozen cells derived from a cell recombinantly expressing a His-tagged thermostable DNA polymerase supplemented with protease inhibitor
 b) digestion of nucleic acids contained in the sample with DNAse I
 c) chromatographic separation using a nickel loaded SEPHAROSE matrix
 d) chromatographic separation using an anion exchange matrix, which is preferably Q-SEPHAROSE ff.

As it is obvious for a person skilled in the art, a dialysis step may be performed after each chromatographic elution, if required. In particular, such a dialysis is particularly advantageous in order to transfer the purified thermostable DNA polymerase into an appropriate storage buffer. A suitable buffer system for long term storage at −20° C. is 20 mM Tris/HCl, 0.1 mM EDTA, 100 mM potassium chloride, 1 mM DTT, 50% glycerol, pH 8.0.

The following examples, sequence listing and figures are provided to aid the understanding of the present invention, the true scope of which is set forth in the appended claims. It is understood that modifications can be made in the procedures set forth without departing from the spirit of the invention.

EXAMPLE 1

Purification of Taq DNA Polymerase

Recombinant Taq DNA polymerase was purified to homogeneity from frozen E. coli cells K12LE392 harbouring the plasmids pUBS520 and pT5-Taq. Protein concentrations were measured at 280 nm. A molar extinction factor of 1.64 was used.

Frozen cells (25 gram) were thawed and suspended in 60 ml buffer A (50 mM Tris/HCl, 0.5 mM phenylmethanesulfonyl fluoride (PMSF), 1 mM EDTA, 0.64 µg/ml Leupeptin, pH 8.0). Cells were disrupted using a French pressure cell.

To the solution ammonium sulfate was added (2.4 gr/100 ml). The pH value was readjusted to pH 8.0. Nucleic acids were precipitated by addition of Polymin P. The precipitated nucleic acids were removed by centrifugation (30 min at 5 000 rpm). The clear supernatant was incubated at 75° C. for 15 min. The precipitated proteins were removed by centrifugation (30 min at 5,000 rpm).

To the clear supernatant solution ammonium sulfate was added (10.57 gr/100 ml). The pH value was readjusted to pH 8.0. The solution was applied on a Phenyl SEPHAROSE CL-4B (1.6×12 cm) equilibrated with buffer B (50 mM Tris/HCl, 1 mM EDTA, 1M ammonium sulfate, pH 8.0). The column was washed with buffer B, then with buffer C (50 mM Tris/HCl, pH 8.0) and finally with buffer D (50 mM Tris/HCl, 1 mM EDTA, 20% ethylene glycol, pH 8.0). The enzyme was eluted with a linear gradient of buffer D and buffer D+4 M urea. Fractions containing the enzyme were pooled.

The pool was applied on a Heparin SEPHAROSE column CL-6B (1.6×12.5 cm) equilibrated with buffer E (50 mM Tris/HCl, 0.1 mM EDTA, 100 mM KCl, 5% glycerol, pH 8.0). The column was washed using buffer E. The enzyme was eluted with a linear gradient of buffer E and buffer E+650 mM potassium chloride. Fractions were analyzed by SDS gel electrophoresis and the fractions containing the enzyme were pooled. The pooled fractions were dialyzed against buffer F (10 mM potassium phosphate, 0.1 mM EDTA, 1 mM DTT, 5% glycerol, pH 8.0).

The dialyzed pool was loaded on a HA Ultrogel (Pall, 1.6×8.5 cm). The column was washed with buffer F. The enzyme was eluted with a linear gradient of buffer F and buffer G (500 mM potassium phosphate, 0.1 mM EDTA, 1 mM DTT, 5% glycerol, pH 8.0). The fractions containing the enzyme were pooled and dialyzed against detergent free storage buffer (20 mM Tris/HCl, 0.1 mM EDTA, 100 mM potassium chloride, 1 mM DTT, 50% glycerol, pH 8.0).

EXAMPLE 2

Purification of Delta 288 Taq DNA Polymerase

The recombinant truncated version of Taq DNA polymerase, delta 288 Taq DNA polymerase (see US 20050037412) was purified to homogeneity from frozen E. coli K12XL1 blue cells harbouring the plasnmid pQE80-L. Protein concentrations were measured at 280 nm. A molar extinction factor of 1.117 was used.

Frozen cells (20 gram) were thawed and suspended in 240 mLl buffer A (50 mM sodium phosphate, 300 mM NaCl, 10 mM imidazol. 0.1 mM phenylmethanesulfonyl fluoride (PMSF), 1 mM DTT, pH 8.0). Cells were disrupted using a French pressure cell.

To the solution, MgCl$_2$ was added to a final concentration of 4 mM. After addition of DNase (50 u/ml) the solution was incubated at room temperature for 30 min. The solution was incubated at to 72° C. for 30 min. After cooling the solution to 2-8° C., the precipitated proteins were removed by centrifugation (10 min at 13 000 rpm).

The clear supernatant was applied to a nickel-loaded chelating SEPHAROSE ff column (5×4 cm) equilibrated in buffer B (50 mM sodium phosphate, 300 mM NaCl, 10 mM imidazole, pH 8.0). The enzyme was eluted in with a linear gradient of buffer B and buffer C (50 mM sodium phosphate, 300 mM NaCl, 250 mM imidazole, pH 8.0). Fractions were analyzed by SDS gel electrophoresis and the fractions containing the enzyme were pooled.

After dialysis against buffer D (25 mM Tris/HCl, 1 mM EDTA, 15 mM NaCl. 5% glycerol, pH 8.5) the solution was applied on a Q-SEPHAROSE ff column (1.6×4 cm). After washing the column with buffer D, the enzyme was eluted using a linear salt gradient (15-200 mM NaCl). Fractions were analyzed by SDS gel electrophoresis and the fractions containing the enzyme were pooled.

The final pool was dialysed against detergent-free storage buffer (20 mM Tris/HCl, 0.1 mM EDTA, 1 mM DTT, 100 mM potassium chloride, 50% glycerol, pH 8.0).

EXAMPLE 3

Preparation of Delta 288 AptaTaq DNA Polymerase

Purified delta 288 Taq DNA polymerase (see Example 1) was blended with aptamer.

The sequence of the aptamer was:

(SEQ ID NO: 2)
CGA TCA TCT CAG AAC ATT CTT AGC GTT TTG TTC TTG TGT ATG ATC G-PO$_4$

A highly concentrated enzyme solution was blended with aptamer and diluted with detergent-free storage buffer to final concentrations of 50 U/μl polymerase and 4.33 pmol aptamer/unit of polymerase.

Additionally, a version having a volume activity of 5 U/μl was produced in the same way. The enzyme blends were stored at −20° C.

EXAMPLE 4

Test of Polymerase Activity

DNA polymerase activity was determined in a primer extension assay using standard procedures. A primer/template hybrid was used as substrate. The primer/template consisted of M13 sequencing primer 5'-GTA AAA CGA CGG CCA GT-3' (SEQ ID No: 1) hybridized to M13 mp9ss DNA template. The primer was extended by the incorporation of dNTPs. The dNTPs mix contained radioactively labeled α$^{32}$dCTP. The synthesized product was precipitated with TCA and the incorporated α$^{32}$dCTP was quantified using a scintillation counter.

Reactions were carried out in a 50 μl volume containing the following reagents: 67 mM Tris (pH 8.3), 5 mM MgCl$_2$, 10 mM mercaptoethanol, 0.2% polydocanol, 0.2 mg/ml gelatine, 200 μM dATP, 100 μM dCTP, 200 μM dGTP. 200 μM dTTP, DNA/primer hybrid (1 μg DNA, 0.3 μg primer) and α$^{32}$dCTP (1 μC). Aliquots of diluted enzyme were added to the mix, mixed and incubated for 60 min at 65° C. After incubation the samples were placed on ice and DNA was precipitated with 10% TCA solution. Samples were filtered through GFC-filters (Whatman), the filters were washed three times with 5% TCA, dried and counted in a β-counter in 2 ml scintillation fluid.

EXAMPLE 5

Amplification of Human Genomic DNA Using Different DNA Polymerase Formulations

A fragment of the tPA gene was amplified from human genomic DNA (Roche Applied Science, Mat. No. 11 691 112). Detection and quantification of the amplified products was done using FRET hybridization probes (U.S. Pat. No. 6,174,670).

To demonstrate the effect of detergents, a preparation of delta 288 Taq DNA polymerase prepared without detergents according to Example 2, a preparation of delta 288 AptaTaq DNA polymerase according to Example 3 and a preparation of Taq DNA polymerase prepared with 0.5% TWEEN 20 were used. Three different polymerase formulations were as follows:

Formulation 1: delta 288 AptaTaq DNA polymerase without detergent

Formulation 2: delta 288 Taq DNA polymerase without detergent

Formulation 3: delta 288 Taq DNA polymerase with detergent (0.5% TWEEN 20)

The following oligonucleotide primers were used:

(SEQ ID NO: 3)
tPA7reverse: GGA AGT ACA GCT CAG AGT TCT (SEQ ID NO: 4)
tPA7forward: CTC CAT TCA TTC TCA AAA GGA CT The detection oligonucleotides were:

tPA Fluos:
(SEQ ID NO: 5)
GGG AAA GGC GGG GTG G-Fluo tPA LC-Red 640:
(SEQ ID NO: 6)
LC-Red 640-GCC ACT TAC CCT CAG AGC AGG CA Reactions (20 μl) were carried out in 384-well plates on a LIGHTCYCLER LC480 platform (Roche Applied Science Cat. No: 05 015 278 001). 2.95 units of the respective polymerase were used per reaction of 20 μl.

The final concentrations of the reagents were:

| | |
|---|---|
| Tris/HCl | 30 mM |
| MgCl$_2$ | 3.2 mM |
| KCl | 30 mM |
| dATP | 0.2 mM |
| dCTP | 0.2 mM |
| dGTP | 0.2 mM |
| dUTP | 0.6 mM |
| Casein | 0.5 g/l |
| tPA7 forward | 0.5 μM |
| tPA7 reverse | 0.5 μM |
| tPA7 Fluos | 0.2 μM |
| tPA7 Red640 | 0.2 μM |
| Human genomic DNA | 0.03 ng-300 ng |

The following cycling program was used on the LC 480 instrument:

| 1. Denaturation | |
|---|---|
| Cycles 1 | |
| Analysis Mode none | |
| Temp. Targets | Segm. 1 |
| Target (° C.) | 95 |
| Acquisition Mode | none |
| Hold (hh:mm:ss) | 00:00:30 |
| Ramp Rate (° C./s) | 4.8 |
| Acquisition (per ° C.) | |
| Sec. Target (° C.) | 0 |
| Step Size (° C.) | 0.0 |
| Step Delay (cycles) | 0 |

| 2. Amplification | | | |
|---|---|---|---|
| Cycles 45 | | | |
| Analysis Mode Quantification | | | |
| Temp. Targets | Segm. 1 | Segm. 2 | Segm. 3 |
| Target (° C.) | 95 | 60 | 72 |
| Acquisition Mode | none | single | none |
| Hold (hh:mm:ss) | 00:00:10 | 00:00:15 | 00:00:20 |
| Ramp Rate (° C./s) | 4.8 | 2.5 | 4.8 |
| Acquisition (per ° C.) | | | |
| Sec. Target (° C.) | 0 | 0 | 0 |
| Step Size (° C.) | 0.0 | 0.0 | 0.0 |
| Step Delay (cycles) | 0 | 0 | 0 |

| 3. Cooling | |
|---|---|
| Cycles 1 | |
| Analysis Mode none | |
| Temp. Targets | Segm. 1 |
| Target (° C.) | 40 |
| Acquisition Mode | none |
| Hold (hh:mm:ss) | 00:00:30 |
| Ramp Rate (° C./s) | 2.5 |
| Acquisition (per ° C.) | |
| Sec. Target (° C.) | 0 |
| Step Size (° C.) | 0.0 |
| Step Delay (cycles) | 0 |

The following table shows the calculated crossing points obtained for the three different polymerase formulations studied:

A low crossing point number corresponds to a high degree of amplified nucleic acid.

| ng template/reaction | 300 | 30 | 3 | 0.3 | 0.03 |
|---|---|---|---|---|---|
| Delta 288 Apta Taq without detergent: | 21.5 | 24.9 | 28.2 | 31.6 | 35.2 |
| Delta 288 Taq without detergent | 22.8 | 26.7 | 29.5 | 30.6 | 32.5 |
| Delta 288 with detergent | 23.7 | 27.9 | 31.0 | 33.3 | 34.1 |

The results demonstrate that with exception of using Delta 288 Apta Taq without detergent in conjunction with minimal amounts of template DNA, the amplification reaction is improved in the absence of a detergent such as TWEEN 20.

EXAMPLE 6

The experiment was basically carried out as disclosed in Example 5 with the exception that the activity of different Taq DNA Polymerase formulations were tested:
A) a polymerase formulation prepared without detergents according to Example 1 (see FIG. 1)
B) a polymerase formulation prepared without detergents according to Example 1, but finally supplemented with NONIDET NP-40 and TWEEN 20; each 0.5% detergents (see FIG. 2)
C) a polymerase formulation prepared with detergents (Roche Applied Science Cat. No. 11 146 165 001) (see FIG. 3).

Figure 1:
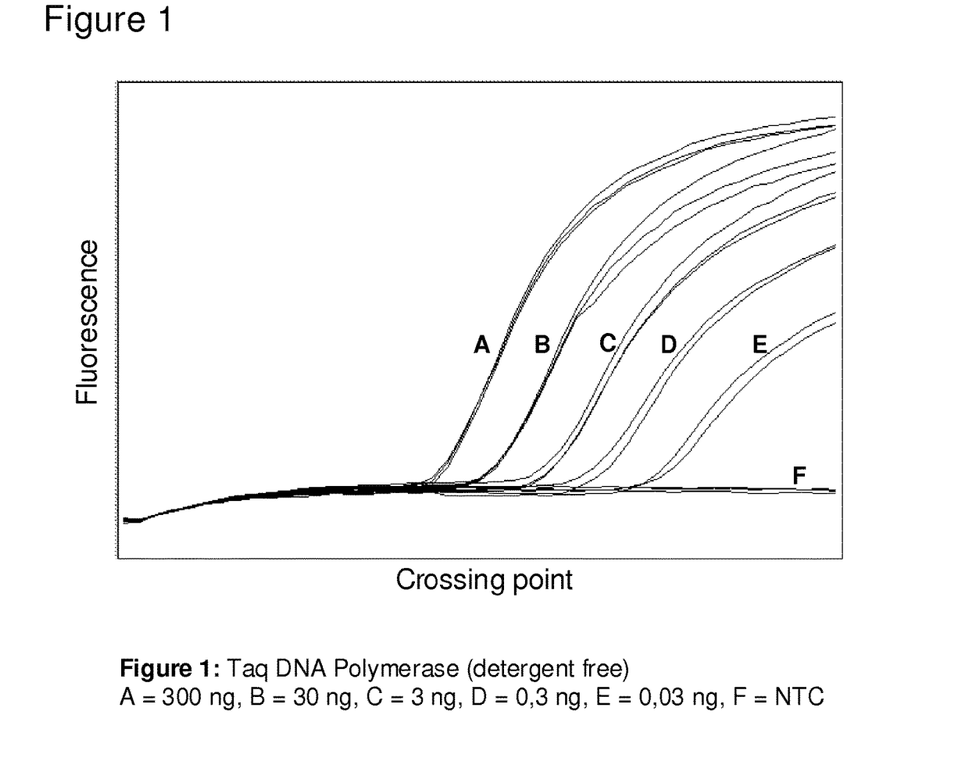
FIG. 1: Result of experiment as disclosed in Example 6. Target DNA was used in various amounts and titrated from 300 ng (A) 30 ng (B). 3 ng (C), 0.3 ng (D) 0.03 ng (E) and no DNA (F). The Taq DNA polymerase used was prepared without the addition of detergents.
Figure 2:
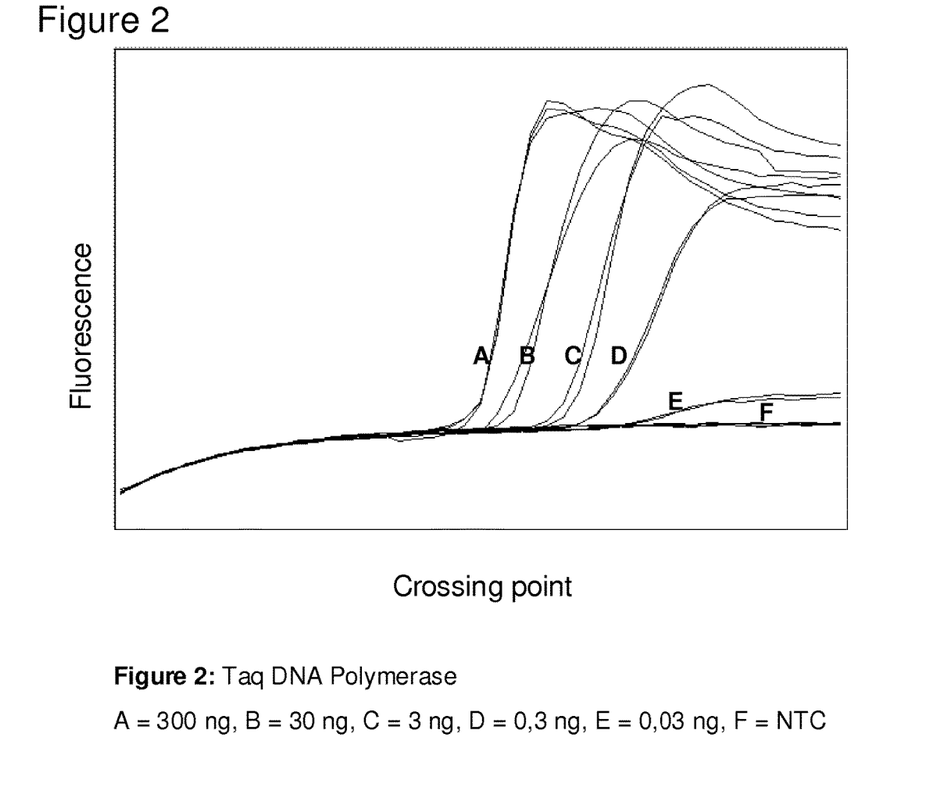
FIG. 2: Result of experiment as disclosed in Example 6. Target DNA was used in various amounts and titrated from 300 ng (A) 30 ng (B). 3 ng (C), 0.3 ng (D) 0.03 ng (E) and no DNA (F). The Taq DNA polymerase used contained detergents (0.5% TWEEN 20, 0.5% NONIDET NP-40).
Figure 3:
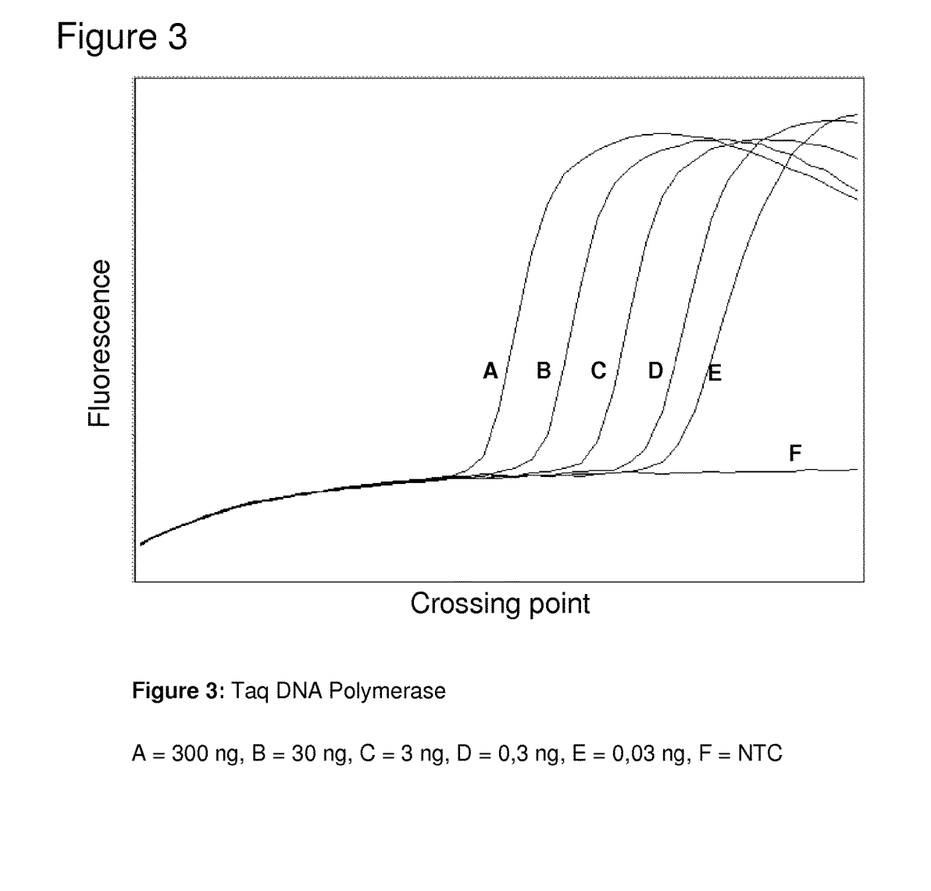
FIG. 3: Result of experiment as disclosed in Example 6. Target DNA was used in various amounts and titrated from 300 ng (A) 30 ng (B). 3 ng (C), 0.3 ng (1)) 0.03 ng (E) and no DNA (F). The Taq DNA polymerase Roche Applied Science Cat. No: 11 146 165 001 was used for this experiment.

The results as shown in FIGS. 1-3 which represent real time PCR amplification curves demonstrate, that good amplification signals are obtained with each of the 3 different formulations. Thus it can be concluded that the performance of Taq DNA polymerase neither requires the presence of detergents during the amplification reaction itself, nor does the addition of detergents during the purification procedure result in an improved performance of the enzyme.

The latter 2 formulations did show a characteristic hook effect for all concentrations of target DNA tested (see FIGS. 2 and 3), i.e., the amplification signal decreased again at late amplification cycles. In contrast, the polymerase prepared without the addition of detergents did not show any hook effect at all (see FIG. 1). It can be concluded that the hook effect observed with formulation B) is predominantly due to the presence of detergents, and, similarly the hook effect in formulation C) is due to the presence of trace amounts of detergents still present within the assay because detergents that have been used during the purification of the Taq DNA polymerase. Thus, the hook effect is only avoided if a polymerase according to the present invention is used, when amplification is performed in the absence of any detergent.

The invention claimed is:

1. A method for amplifying DNA, comprising the steps of:
providing a detergent-free assay mixture substantially free of a non-functional mutated DNA polymerase, said mixture comprising:
   a Taq DNA polymerase which is not attached to a non-peptide polymer and that has never been exposed to a detergent, wherein the Taq DNA polymerase is a Taq DNA polymerase selected from the group consisting of: a full-length Taq DNA polymerase and a Delta 288 Taq DNA polymerase;
   a pair of complementary oligonucleotide primers;
   a first detection oligonucleotide labeled with a fluorescent donor probe; and
   a second detection oligonucleotide labeled with a fluorescent acceptor probe;
   wherein the fluorescent donor and said fluorescent acceptor are capable of exchanging energy;
conducting a polymerase chain reaction with said detergent-free assay mixture; and
monitoring the change in the fluorescence as the polymerase chain reaction occurs.

2. The method according to claim 1, wherein the fluorescent donor probe is fluorescein.

3. The method according to claim 1, wherein the Taq DNA polymerase is a full length Taq DNA polymerase.

4. The method according to claim 1, wherein the Taq DNA polymerase is a Delta 288 Taq DNA polymerase.

* * * * *

SEQUENCE LISTING

<160> NUMBER OF SEQ ID NOS: 6

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gtaaaacgac ggccagt                                                 17

<210> SEQ ID NO 2
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3'-PO4

<400> SEQUENCE: 2
cgatcatctc agaacattct tagcgttttg ttcttgtgta tgatcg                  46

<210> SEQ ID NO 3
<211> LENGTH: 21
<212> TYPE: DNA
<213> ORGANISM: Artificial Sequence -continued

```
<220> FEATURE:
<223> OTHER INFORMATION: Description of Artificial Sequence: Synthetic
      primer

<400> SEQUENCE: 3
ggaagtacag ctcagagttc t                                              21

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctccattcat tctcaaaagg act                                            23

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3'-Fluo

<400> SEQUENCE: 5
gggaaaggcg gggtgg                                                    16

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-LC-Red 640

<400> SEQUENCE: 6
gccacttacc ctcagagcag gca                                            23
```